(«12») United States Patent
Bouchier et al.

(10) Patent No.: US 6,916,377 B2
(45) Date of Patent: Jul. 12, 2005

(54) SEMI-AUTOMATIC COATING SYSTEM APPARATUS

(75) Inventors: Mark S. Bouchier, Lakeville, MN (US); Robert E. Lund, St. Michael, MN (US); James A. Gohman, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 12 days.

(21) Appl. No.: 10/311,646

(22) PCT Filed: Jul. 30, 2001

(86) PCT No.: PCT/US01/23699

§ 371 (c)(1),
(2), (4) Date: Jul. 15, 2003

(87) PCT Pub. No.: WO02/09786

PCT Pub. Date: Feb. 7, 2002

(65) Prior Publication Data

US 2004/0033306 A1 Feb. 19, 2004

Related U.S. Application Data

(62) Division of application No. 09/630,175, filed on Aug. 1, 2000, now Pat. No. 6,534,112.

(51) Int. Cl.$^7$ ................................................ B05C 3/02
(52) U.S. Cl. ..................... 118/407; 118/429; 422/296; 422/297; 134/166 R
(58) Field of Search ................................ 118/407, 429; 623/1.46, 1.48; 427/2.24, 2.25, 2.28; 422/33, 38, 295–297, 301; 134/66, 79, 166 R (56) References Cited

U.S. PATENT DOCUMENTS

| 3,893,843 | A | * | 7/1975 | Fry et al. ..................... 134/10 |
|---|---|---|---|---|
| 4,001,460 | A | | 1/1977 | Kinney et al. |
| 4,308,363 | A | | 12/1981 | Vaughn |
| 4,710,233 | A | * | 12/1987 | Hohmann et al. ........... 205/701 |
| 5,188,670 | A | | 2/1993 | Constantz |
| 5,217,493 | A | | 6/1993 | Raad et al. |
| 5,505,218 | A | * | 4/1996 | Steinhauser et al. ........ 134/95.1 |
| 5,624,704 | A | | 4/1997 | Darouiche et al. |
| 5,667,753 | A | * | 9/1997 | Jacobs et al. .................. 422/29 |
| 5,756,145 | A | | 5/1998 | Darouiche |
| 5,851,485 | A | * | 12/1998 | Lin et al. ....................... 422/33 |
| 5,853,745 | A | | 12/1998 | Darouiche |
| 5,871,692 | A | * | 2/1999 | Haire et al. .................... 422/28 |
| 5,902,283 | A | | 5/1999 | Darouiche et al. |

(Continued)

FOREIGN PATENT DOCUMENTS

| FR | 90 06984 | 12/1991 |
|---|---|---|
| FR | 98 14001 | 5/1999 |

OTHER PUBLICATIONS

Brook et al, Inhibizone Treatment: The First Antibiot Treatment Impregnated into the Tissue–Contacting Surface of an Inflatable Penile Prosthesis, AUA 2001 Publishing ID: 1047, 1 page (2001).

(Continued)

*Primary Examiner*—Laura Edwards
(74) *Attorney, Agent, or Firm*—Jose' W. Jimenez (57) ABSTRACT

A semi-automated coating system for providing medical devices with antimicrobial coatings is disclosed. The semi-automated coating system extends the coating solution's usable life span by minimizing exposure to light, air and temperature extremes. Moreover, the disclosed semi-automated coating system minimizes operator and environmental exposure to the coating solutions. Methods disclose techniques for preparing coating solutions, setting up the coating system and operating the device. Moreover, the systems and methods described herein minimize operator intervention with the coating processes and provide superior product consistency.

13 Claims, 7 Drawing Sheets

U.S. PATENT DOCUMENTS

| | | | |
|---|---|---|---|
| 6,001,425 A | 12/1999 | Stash et al. | |
| 6,129,928 A | * 10/2000 | Sarangapani et al. | 424/423 |
| 6,162,487 A | 12/2000 | Darouiche | |
| 6,254,921 B1 | 7/2001 | Chappa et al. | |

OTHER PUBLICATIONS

Darouiche et al. Efficacy of Antimicrobial–Impregnated Bladder Catheters in Reducing Catheter–Associated Bacteriuria: A Prospective, Randomized, Multicenter Clinical Trial, Urology, v. 54, pp. 976–981 (1999).

Li H et al, Antibacterial Activity of Antibiotic Coated Silicone Grafts, Journal of Urology, v. 160, pp. 1910–1913 (Nov. 1998).

Raad et al, Antibiotics and Prevention of Microbial Colonization of Catheters, Antimicrobial agents and chemotherapy, v. 39(11), pp. 2397–2400 (Nov. 1995).

Raad et al, The Broad–Spectrum Activity and Efficacy of Catheters Coated with Minocycline and Rifampin, Journal of Infectious Disease 1996, v. 173, pp. 418–424.

Raad et al, Central Venous Catheters Coated with Monocycline and Rifampin for the Prevention of Catheter–Related Colonization and Bloodstream Infections: A Randomized, Double–Blind Trial, Internal Med 1997, v. 127, No. 4, pp. 267–274.

Antibiotic Surface Treatment and Indewelling Medical Devices, American Medical Systems Brochure, 2001.

* cited by examiner

SEMI-AUTOMATIC COATING SYSTEM APPARATUS

This application is a National Stage under 35 USC 371 of International Patent Application No. PCT/US01/23699, filed Jul. 30, 2001, SEMI-AUTOMATIC COATING SYSTEM AND METHODS FOR COATING MEDICAL DEVICES. This application is a division of and claims the benefit of U.S. patent application Ser. No. 09/630,175, filed Aug. 1, 2000, now U.S. Pat. No. 6,534,112, entitled "SEMI-AUTOMATIC COATING SYSTEM METHODS FOR COATING MEDICAL DEVICES".

FIELD OF THE INVENTION

The present invention generally relates to methods and systems for coating medical devices. Specifically, the present invention relates to systems and methods for automating batch processing of medical devices in a closed system. More specifically, the present invention provides semi-automated methods and systems for coating implantable medical devices with antimicrobials using closed systems that maintain coating solution integrity, increase product throughput and minimizes personnel and environmental exposure to the coating solution.

BACKGROUND OF THE INVENTION

Localized and systemic infections represent one of the most serious post surgical complications. Over the past fifty years tremendous advances in materials, training and antimicrobial therapies have significantly reduced the number of life-threatening post operative infections. The development of pre-sterilized disposable surgical dressings, medical instruments, gowns, drapes and other materials have helped reduce infection frequency. However, the development of improved antimicrobials represents the single most significant advance in infection control.

There are essentially three categories of antimicrobial agents: antiseptics, disinfectants and antibiotics. Antiseptics are generally defined as compounds that kill or inhibit the growth of microorganisms on skin or living tissue. Antiseptics include, but are not limited to, alcohols, chlorhexidine, iodophors and dilute hydrogen peroxide. Disinfectants are compounds that eliminate pathogenic microorganisms from inanimate surfaces and are generally more toxic, and hence more effective, than antiseptics. Representative disinfectants include, but are not limited to, formaldehyde, quaternary ammonium compounds, phenolics, bleach and concentrated hydrogen peroxide. Antibiotics are compounds that can be administered systematically to living hosts and exhibit selected toxicity, that is, they interfere with selected biochemical pathways of microorganisms at concentrations that do not harm the host. In the alternative, an ideal antibiotic will target specific metabolic pathways that are essential for the parasite, but absent in the host. Antibiotics generally work using one of four basic mechanisms of action: 1) inhibition of protein synthesis; 2) inhibition of cell wall synthesis; 3) interference with nucleic acid synthesis; and 4) altering cell membrane selective permeability. Antibiotics include, but are not limited to penicillins, aminoglycosides, tertacyclines and macrolides, The fundamental difference between antiseptics, disinfects and antibiotics is the ability of microorganisms to develop resistance to antibiotics. The characteristics that make antiseptics and disinfectants so effective generally precludes the development of resistant microorganisms. However, disinfectants are unsuitable for use on living tissues and many antiseptics are primarily limited to localized, generally topical, applications. Consequently, most antimicrobial prophylactic and therapeutic regimens rely on antibiotics.

The microorganism's susceptibility to an antimicrobial and the ability of the antimicrobial to reach the infection site are the two most significant factors that determine antimicrobial therapy efficacy. Antimicrobial susceptibility is generally determined by culturing the organism in the laboratory and testing it against a panel of candidate drugs. However, laboratory testing can only be done if the agent causing the infection is known. When antibiotics are used prophylactically, as is the case with surgical patients, physicians generally prescribe drugs targeted to suppress the growth of the most common post surgical infectious agents. One of the most common organisms associated with surgical infections is *Staphylococcus aureus*. In the past, penicillin class drugs were considered the drugs of choice to thwart *S. aureus* infections. However, recently, many new antibiotic resistant microorganisms including penicillin resistant *S. aureus* have emerged making post surgical infection control even more challenging. Consequently, physicians have turned to new generations of antibiotics in response to emerging resistant strains.

Until recently, methicillin, an analogue of penicillin, was the preferred drug for treating and preventing penicillin resistant *S. aureus* infections. However, methicillin resistant *S. aureus* (MRSA) are becoming increasingly more common. Therefore, newer and more effective treatments for MRSA as well as other difficult to treat post surgical infections are in great demand.

One approach to treating and preventing the emergence of antibiotic resistant bacteria such as MRSA is to use two or more antimicrobial compounds in combination. The advantages to this approach include having a second antimicrobial present to inhibit resistant sub-population emergence during treatment and the potential for antimicrobial synergy. Antimicrobial synergy occurs when the efficacy of one antimicrobial is enhanced by another such that the total antimicrobial effect is greater than either one alone. In many cases either antimicrobial used separately may not completely eradicate the infection, but when the drugs are used in combination, powerfully efficacious antimicrobial regimens result.

However, even the most sensitive microorganisms cannot be killed by antimicrobials unless they can reach the infection site (antimicrobial bioavaliablity). Numerous factors determine antimicrobial bioavailablity including route of administration, clearance rates from the body, tissue solubility, and the degree of blood flow surrounding the infected site. Antimicrobials that are susceptible to destruction by digestive fluids, or drugs not easily absorbed in the intestines, must be administer parenterally (usually intravenously). However, regardless of the administration route, the antibiotic must survive circulation through the blood stream prior to reaching the treatment site. If the liver or kidneys rapidly removes an antimicrobial from the blood stream, or if the antimicrobial has a high affinity for blood proteins such that it is bound and inactivated by the blood, its bioavailability can be significantly reduced. This is especially true if the infection site is deep within tissues or organs that have minimal blood flow.

Deep tissue infections can result when medical implants become contaminated prior to surgical placement. When oral or parenterally administered antimicrobials fail to effectively control and eliminate the infection, the medical implant may have to be removed. Removal requires additional surgical procedures to treat the infection and re-implant the device after the infection completely resolves. Moreover, once deep tissue infections are established, long term antimicrobial therapy and hospitalization may be required. These additional procedures increase the costs associated with device implantation, subject the patient to discomfort and in rare circumstances, increase the threat of permanent disfigurement.

Coating implantable medical devices with antimicrobial compounds provides a technique for deep tissue drug delivery that can significantly reduce the risk of post implantation infections. Coating procedures should employ broad spectrum antimicrobials that are effective against most post surgical infections, especially MRSA infections. The antimicrobials need to be soluble in physiological fluids and must be stable enough to survive processing steps required to successfully coat the medical device. Ideally, a synergistic antimicrobial combination should be used. Non-limiting examples of antimicrobial combinations are described in U.S. Pat. Nos. 5,624,704 and 5,902,283, the entire contents of which are herein incorporated by reference. Moreover, the antimicrobial coating procedure must employ methods and materials that are compatible with the antimicrobial and the material used to make the medical device. Medical devices, specifically implantable types, can be fabricated from a wide variety of biocompatible compounds including metals and polymers. Each material presents its own unique challenges to material scientists when it is necessary, or desirable, to coat medical devices with bioactive materials. However, all coating methodologies share common objectives including the need to maximize expensive and labile coating solutions, minimize environmental contamination, provide the medical device with an even coating, and maintain an efficient, controlled process that complies with Federal Food and Drug Administration (FDA) Good Manufacturing Practices (GMP). Tedious manual methods of batch coating medical devices cannot achieve these goals for all medical devices on a consistent basis.

The size, shape and composition of the medical devices can significantly limit manual methods. Moreover, lot-to-lot consistency, GMP compliance and product throughput are all greatly enhanced when automated, or semi-automated, processes are involved. Moreover, non-automated processes subject expensive coating solutions to contamination and excessive waste resulting from spillage and product handling. Additionally, many polymeric compounds used to make medical devices are coated using harsh and often toxic solvent mixtures in order to imbibe the coating material into the devices. Exposure to these solvents poses a potential risk to personal, equipment and the environment that can be best minimized by coating in a closed system, a process incompatible with most manual methods.

Therefore, there is a need for methods and systems that can provide implantable medical devices with antimicrobial coatings. Moreover, there is a need for methods and systems that can provide antimicrobial coatings in a closed system that reduce exposure to toxic solvents, maintain coating solution integrity for prolonged periods, allow for maximum product throughput, provide the medical device with a consistent, even coating, minimize product handling and accomplishes these goals in an FDA GMP compliant manner.

SUMMARY OF THE INVENTION

It is an object of the present invention to provide a self-contained, automated system for coating a medical device with a antimicrobials.

It is another object of the present invention to provide antimicrobial coating systems and methods that extend the usable life expectancy (pot life) of the coating solution by limiting the solution's exposure to atmospheric conditions including light and air.

It is still another object of the present invention to provide antimicrobial coating systems and methods that extend the pot life of the coating solution by minimizing thermal exposure.

It is another object of the present invention to provide antimicrobial coating systems and methods that protect the operator and the environment from the coating solution.

It is yet another object of the present invention to provide antimicrobial coating systems and methods that are automated and minimize user intervention.

It is another object of the present invention to provide implantable medical devices having antimicrobial coatings that reduce post implantation infections by releasing antimicrobial compounds into the surrounding tissues for sustained time periods.

The coating solutions of the present invention are composed of antimicrobial compounds including, but not limited to, antiseptics and antibiotics dissolved in potentially toxic organic solvents. These solutions are extremely expensive to prepare and are easily inactivated by exposure to temperatures above ambient, air (specifically reactive oxygen species), light (specifically ultraviolet light) and contamination. Therefore, maximizing the pot life requires precise temperature control and protection from air, light and contamination. The methods and systems of the present invention accomplish these and other goals and simultaneously reduce the manufacturing environment's exposure to potentially toxic coating solutions. (It is important to distinguish the coating solutions from coated medical devices. The coating solutions of the present invention are highly concentrated mixtures of antimicrobial compounds and solvents. These mixtures may be toxic to manufacturing professionals exposed to large concentrations. However, the coated medical device, when used in accordance with the manufacturer's directions for use and under the supervision of a qualified physician, present minimal or no risks to the patient).

The present invention provides methods and systems that permit medical devices to be safely coated with antimicrobial compounds while maximizing pot life. However, the systems and methods of the present invention can be used to coat any device safely and efficiently with a wide range of different compounds and are not limited solely to providing medical devices with antimicrobial coatings.

The use of the term "coating" is not intended as a limitation and includes any physical or chemical method of providing the surfaces, or polymeric matrices, of medical devices with antimicrobial properties. Non-limiting examples of such chemical and physical methods include impregnation, imbibing, ionic interactions, covalent bonds, van der Waals forces, hydrogen bonding, protein-protein interactions, antibody-antigen complexes, resin coatings, electrodeposition, plasma deposition or the like. Hence the term coating is not to be construed narrowly to mean merely a surface layer, but should be interpreted to include providing a homogeneous concentration or gradient of antimicrobials throughout a medical device's body.

The present inventors have determined that optimum coating of medical devices occurs when the coating solution is heated to temperatures that significantly accelerate the degradation of the coating solution. In order to optimize the coating process and simultaneously maximize the solution's pot life, the coating solutions of the present invention are preheated in a holding vessel before being transferred to a processing vessel containing the medical devices. Any coating solution remaining in the holding vessel is cooled to ambient temperatures or below while the processing vessel containing the antimicrobial solution and medical device is held at a constant elevated temperature. At the conclusion of a predetermined optimum processing time, the coating solution is transferred from the processing vessel back to the holding vessel where it is cooled to ambient temperatures or below. This entire process is conducted in a sealed system that protects the coating solution from exposure to damaging environmental factors, reduces solvent evaporation and isolates manufacturing personnel from the solution.

After the medical device has been coated it is aerated for a predetermined time period using a pressurized gas flow (sparging system) and then washed at least once using a wash solution that is pumped into the closed processing vessel and gently agitated using the sparging system of the present invention. After washing is completed, a gas, usually air, is passed over the medical device using the sparger to accelerate the drying process. The device is then removed from the sealed system and packaged prior to terminal sterilization.

The entire process of the present invention is under the control of a programmable microprocessor/controller that receives a series of imputes from remotely located sensors. Each sensor monitors an event and continually notifies the microprocessor/controller of its status. Should any sensor detect an out-of-range condition, the system will either fail to initiate the next step or abort the process while simultaneously notifying an operator of a default situation.

In one embodiment of the present invention the self-contained coating system is attached to a containment platform to collect and confine accidental coating solution spills. Attached to the containment platform is at least one temperature controller consisting of either a heater, a chiller or a combination thereof, a holding vessel a processing vessel and at least one fluid transfer system. The fluid transfer system moves coating solution between the holding and the processing vessels and/or wash solution to and from the processing vessel. In one embodiment of the present invention there are a plurality of fluid transport systems each directing the flow of different fluids between the holding vessel and processing vessel and/or fluid reservoirs.

In one embodiment of the present invention the holding and processing vessels are fitted with sealable closures and at least one mixing device for maintaining uniform antimicrobial solution and for preventing thermal gradients from forming. The processing vessels of the present invention are also fitted with a sparging system that provides a gas flow into the processing tank during the aeration, washing and drying steps. In one embodiment of the preset invention the gas flow velocity may be adjusted to optimize the particular process step.

In another embodiment of the present invention the antimicrobial coating system includes one or more valve assemblies located at various points along the fluid transfer systems and gas lines. Additionally, numerous sensors may be located on the holding vessel, the processing vessel, vessel closures, the heat transfer devices, the fluid transfer systems, and temperature controllers. Each sensor feeds information to a programmable microprocessor that controls contents, temperatures, fluid levels, and gas flow within the holding and processing vessels. The programmable microprocessor of the present invention can also be adapted to open and close valves and act as a fail-safe monitor responsive to remote sensors.

In another embodiment of the present invention a method for coating a medical device is provided. This method includes providing a sealable first vessel filled with a coating solution and a sealable second vessel containing a medical device to be coated. The coating solution in the first vessel is preheated to a temperature appropriate for the coating process and then transferred to the second preheated vessel. Any coating solution remaining in the first vessel is cooled to at least ambient temperature and the coating solution in the second vessel is held at a constant coating process temperature until the processing interval is complete. At the conclusion of the processing interval the coating solution in the second vessel is transferred back to the first vessel and cooled.

The coated medical device is then aerated, after which the wash solution is transferred into the second vessel and the medical device is washed while gas is gently sparged into the wash solution. After a predetermined period the wash solution is removed and the wash step is repeated as many times as desired. After washing is complete the medical device is dried using a higher velocity of sparged gas. The entire method can be automated by providing a microprocessor/controller responsive to at least one remote sensor.

Other objects and features and advantages of the present invention will be apparent to those skilled in the art from a consideration of the following detailed description of preferred exemplary embodiments thereof taken in conjunction with the Figures which will first be briefly described.

DETAILED DESCRIPTION OF THE INVENTION

Deep tissue infections associated with in vivo medical devices occasionally occur when a medical device is accidentally contaminated with pathogenic or opportunistic microorganisms prior to implantation. Accidental contamination can occur if the integrity of the product packaging is compromised after terminal sterilization, or if the product contacts a contaminated surface after being removed from its packaging immediately prior to implantation. If the contaminated medical device is implanted, the microorganism may begin to proliferate in the tissues surrounding the implanted device, resulting in an infection.

Generally, systemic antibiotics are administered prior to surgery and continued for an additional seven days or more. However, systemic antibiotics may not always prevent the establishment of deep tissue infections. For example, an organism will continue to multiply unabated if it is resistant to the antibiotics being administered, or if the antibiotic does not reach the infection site in concentrations required to kill the organism. Recently, temporary medical devices such as catheters having antimicrobial coatings that are released in effective concentrations for sustained periods have been employed to help prevent post implantation infections. However, the antimicrobial coating solutions used are extremely expensive and generally require coating procedures that rely on elevated temperatures and toxic solvents in order to obtain uniform stable coatings.

Standard manufacturing practices rely on batch containing techniques that involve manually transferring the coating solutions into processing tanks and heating the solution to process temperature. The medical devices are immersed in the heated coating solution for a predetermined time and then removed from the processing tank and manually washed. The coating solution is maintained at coating temperatures for the duration of the manufacturing shift and then discarded due to antimicrobial thermal breakdown and solvent evaporation. Consequently, large quantities of antimicrobials and solvents are used each time a medical device batch is coated. The cost and waste associated with batch processing techniques is easily amortized when thousands of small medical devices are coated in a single batch. However, large bulky medical devices that displace large volumes of coating solution cannot be economically coated using batch methods. Moreover, large quantities of potentially toxic solvents are required to batch coat bulky medical devices. This results in increased material and solvent disposal costs, excessive personnel and environmental exposure and reduced product consistency.

The present invention provides methods and systems that significantly extend the useable life span of a coating solution (pot life) and facilitate the safe and efficient processing of large quantities of medical devices. The present invention is particularly well adapted to processing large quantities of bulky medical devices with increased economy and safety.

The term "coating" used herein is not intended as a limitation and is not to be construed as a process that merely covers or saturates a medical device's surface. Rather, the term coating is defined as any method, chemical or physical, that provides a medical device with antimicrobial properties, including, but not limited to, the medical device's exterior surfaces and/or internal matrices.

The coating solutions of the present invention can be used to provide medical devices with antimicrobial properties utilizing a variety of physical and chemical interactions between the device and the coating materials. In one embodiment of the present invention polymeric compounds, such as, but not limited to, silicones, polyolefins and polyesters can be impregnated with the antimicrobial coatings through an imbibing process. Imbibing occurs when a polymer is suspended in a solvent mixture that swells the polymer matrix carrying solutes present in the solvent into the polymer itself. After the polymer has been removed from the solvent the polymer matrix returns to its pre-swollen configuration, trapping solute molecules within the polymer. In the present invention solute molecules include antiseptics and/or antibiotics. Other physical and chemical processes may be used to provide homogeneous concentrations or antimicrobial concentration gradients to medical devices of the present invention. The chemical and/or physical makeup of the medical device dictates the optimum process.

In one embodiment of the present invention antimicrobial compounds are dissolved in organic solvents that swell the polymer causing the antimicrobials to be carried into the polymer matrix, trapping them within after the device is removed from the solvent. The present inventors have determined that this process is particularly valuable when providing delicate thin-walled silicone medical devices with antimicrobial coatings. In one embodiment of the present invention solvent exposure was limited to approximately 30 minutes at a temperature of approximately 35° C. This process impregnates silicone devices with effective amounts of antibiotics while preserving the integrity of the silicone polymer matrix.

The coating system of the present invention is composed of a holding vessel for storing and preheating the coating solution, a processing vessel for coating, aerating, washing and drying medical devices, a fluid transfer system for transporting coating and wash solutions between the vessels and reservoirs, a temperature controller that heats and cools the solutions, a gas sparging system to facilitate aerating, washing and drying, solution mixers and a microprocessor/controller that automates the entire process. In one embodiment of the present invention the entire system is coupled to a containment platform that confines accidental coating solution spills and prevents contamination of the manufacturing environment with potentially toxic solvents.

The present invention can be used to coat medical devices made from any biocompatible material including but not limited to metals and synthetic and natural polymers. Non-limiting examples include stainless steel, nickel, titanium, silver, gold, platinum, aluminum and alloys thereof, natural rubber latex, synthetic latexes, silicone, polyolefins, and polyesters. In one embodiment of the present invention the coating solution is composed of solvents including, but not limited to butyl acetate, methyl alcohol, amyl acetate, benzene, carbon tetrachloride, chloroform, diethyl ether, ethylene dichloride, hexane, 2-ethyl hexanol, hexyl ether, methyl ethyl ketone (MEK), methyl isobutyl ketone, methylene chloride, perchloroethylene, Stoddard solvent (mineral spirits), toluene, trichloroethylene, xylene and combinations thereof.

The solvent chosen must be compatible with the medical device and the antimicrobial. The antimicrobial must be soluble in the solvent system selected and not denatured once dissolved. Polyolefin, polyester and silicone medical devices are generally used with solvent systems that swell the polymer's surface, permitting the solvent to carry the antimicrobial into the polymer's surface (imbibe). However, the solvent should not destroy the polymer's functional characteristics. After the medical device is removed from the solvent/antimicrobial mixture the device is allowed to regain its functional properties during the aeration, washing and drying steps.

In one embodiment of the present invention the medical device is composed of silicone and the solvent system is a butyl acetate and methanol blend. The antimicrobials are first dissolved in the methanol and then the butyl acetate is added; the resulting mixture is used to imbibe the antimicrobial into a silicone medical device. After a predetermine coating interval, the solvent/antimicrobial mixture is removed and the silicone medical devices of the present invention are washed then dried. Silicone medical devices are easily softened when exposed to swelling solvents such as butyl acetate. Immediately after the solvent is removed the silicone devices are extremely fragile and can be easily broken if handled in an aggressive manner.

In one embodiment of the present invention the fragile coated medical devices are aerated using sparged gas immediately after the coating solution has been returned to the holding vessel, the aeration process continues for a predetermined time sufficient to allow structural integrity to return to the polymer. At the conclusion of the aeration process the medical devices of the present invention are washed.

Wash fluids are added to the processing vessel gently to avoid disturbing the devices. In one embodiment of the present invention the washing fluid enters the processing vessel through a port near the vessel top and is deflected downward along the vessel sides. In another embodiment of the present invention the wash fluids slowly fill from the vessel's bottom. Washing is facilitated by sparging a low velocity gas stream into the wash fluid via a sparge system located at the vessel's base. This low velocity gas sparge gently agitates the wash solution to aid in removing excess antimicrobial deposits that accumulated on the product during coating. During the washing process the silicone devices of the present invention continue to regain firmness and become increasingly resistant to tearing and deformation. Final polymer integrity is restored as the medical devices are dried in the processing vessel under a stream of sparged gas.

The present inventors have determined that the aeration, washing and drying processes of the present invention are greatly enhanced when gas is sparged into the processing vessel during these steps. Gas is provided to the process vessel sparger using either compressed gas cylinders or a remote gas compressor. The gas used may be, but is not limited to, air, nitrogen, argon or other minimally reactive gases or gas mixtures. In one embodiment of the present invention the sparger is a spiral shaped device made from stainless steel or other non-reactive alloys and is sealed to the processing tank's bottom. Gas can be passed through the sparger at variable rates controlled by either the microprocessor/controller of the present invention or manually. In one embodiment of the present invention the gas is used at one velocity during aeration and drying steps and a second, lower velocity during the washing step. The gas is vented to the outside through a series of gas lines connected to a valve located near the vessel top. The venting mechanism of the present invention may also provide one or more high-efficiency particulate air (HEPA)/volatile organic compound (VOC) filtration systems.

The antimicrobial solutions used in accordance with the teaching of the present invention are composed of heat labile antimicrobials such as, but not limited to, antibiotics and antiseptics. These labile antimicrobial compounds are extremely expensive and need to be dissolved in volatile solvents including, but not limited to, water, alcohols, ketones, ethers, esters and aldehydes. When batch-coating techniques are employed the coating solutions of the present invention are exposed to above ambient temperature conditions that accelerate the thermal breakdown of the antimicrobials. Moreover, open, or partially sealed, containers are often used to prepare the solutions and coat the medical devices. These containers may expose the coating solution to ultraviolet light and air that further accelerate antimicrobial breakdown and promote volatile solvent evaporation. As the solvents evaporate and the compounds deteriorate, the exact concentration of biologically active coating material changes and the coating solution begins to discolor. Medical devices coated using the deteriorated solutions have unknown biological activity and are cosmetically unattractive. Consequently, the deteriorated coating solution must be destroyed and a new solution prepared before further coating can occur.

In one embodiment of the present invention the coating solution is continuously maintained under an inert atmosphere. After the antimicrobial coating solution has been prepared as described in Example 1 below, an inert gas, such as, but not limited to, bone-dry nitrogen is injected into the holding tank such that air present in the holding tank is displaced through a vent located near the holding vessel's top above the fluid level.

In another embodiment a sparging apparatus is incorporated into the bottom of the holding vessel through which the inert gas is introduced. Inert gas is also provided to the entire coating system including all gas lines, fluid paths, fluid transfer systems and the processing tank. In this embodiment the entire coating system remains under an inert atmosphere until the system is opened to air. The holding vessel containing coating solution is continually maintained in an inert atmosphere and remains sealed until such time as a new batch of coating solution is prepared. As the fluid level within the holding vessel is reduced during coating solution transfer to the process vessel, inert gas is pumped into the holding vessel to prevent a partial vacuum from forming therein. In one embodiment of the present invention inert gas displaced from the filling process vessel is transferred to the emptying holding vessel. In another embodiment inert gas is vented out of the filling process vessel and inert gas is provided to the emptying holding vessel from an inert gas reservoir. However, the process of providing inert gas to emptying vessels and removing insert gas from filling vessels will depend on the coating system configuration and any such processes are considered within the scope of the present invention. Engineers of ordinary skill in the art would be capable of configuring a suitable gas transfer system consistent with the teachings of the present invention.

The coating systems and processes of the present invention provide improved coating solution stability and enhanced operator safety by employing a sealed, semi-automated system having the capacity to maintain coating solutions at temperatures that improve stability, reduce evaporation and prevent atmospheric contamination. The coating solutions of the present invention are heated to coating temperature for a minimum period and then cooled to holding temperature until the next coating cycle is initiated.

Examples of medical devices that can be coated using the systems and methods of the present invention include, but are not limited to, catheters, surgical slings, artificial joints penial implants, ocular implants, stents, suture and heart valves.

Figure 1:
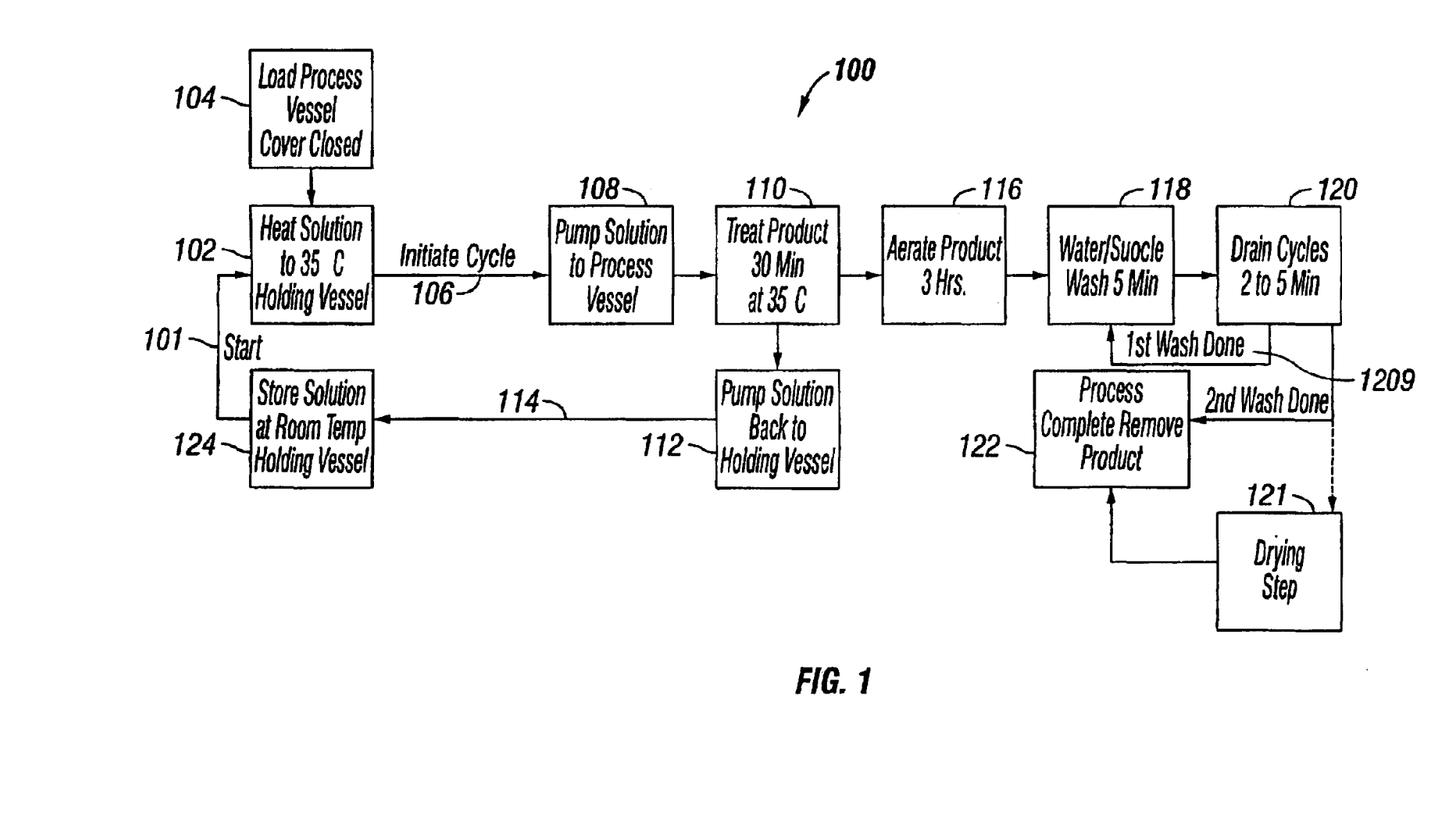
FIG. 1 is a block diagram that depicts the general coating process in accordance with the teachings of the present invention.

FIG. 1 depicts the process 100 of the present invention in a generalized block diagram. The semi-automated process of the present invention begins 101 when the coating solution stored 124 at or below ambient temperature in the holding vessel is heated to process temperature 102. Product is transferred 104 into the processing vessel and the cycle is initiated 106 when the coating solution reaches process temperature. Coating solution is pumped 108 into the holding vessel 108 and the product is coated for a predetermined time 110. Any coating solution remaining in the holding vessel is cooled to ambient temperature or below. At the conclusion of the coating step the coating solution is pumped back into the holding vessel and cooled 112. The coated product remaining in the processing vessel is aerated 116 to provide time for the swollen product matrix to reform, and/or for the coating material to fully imbibe. The product is the washed 118 using a wash solution and gentle agitation from sparged gas. At the completion of the wash step 120 the wash fluid is drained from the processing vessel and the wash step is repeated 120a, or the product is removed from the process vessel and dried 122. In another embodiment of the present invention the product 121 is dried in the processing vessel.

Figure 2:
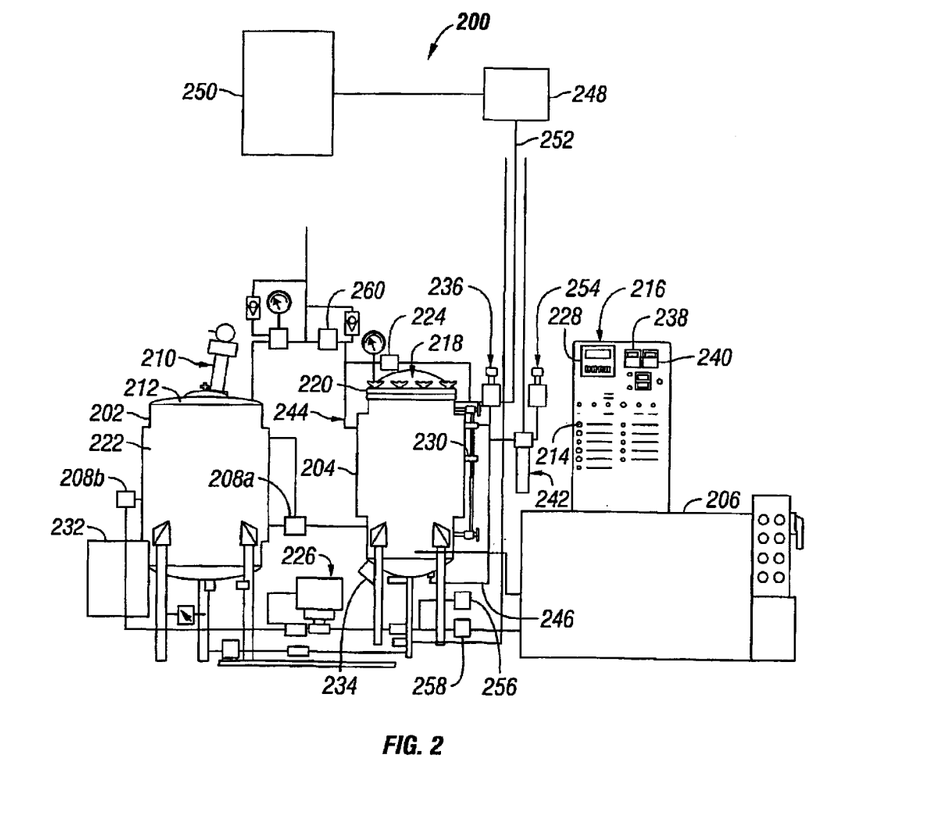
FIG. 2 depicts the basic components of the coating system of the present invention.

Turning now to FIG. 2. The coating system of the present invention is generally depicted at 200 and is composed of a holding vessel 202 for storing the coating solution at or below ambient temperature and for preheating the coating solution to a predetermined process temperature. In one embodiment of the present invention the coating solution is preheated in the holding vessel 202 using a circulating heater 206. The circulation heater 206 cycles a heat transfer fluid through thermal jackets that envelop holding vessel 202 and processing vessel 204. Circulation control valves 208a and 208b facilitate heat transfer fluid circulation. The coating solution in holding vessel 202 is continually mixed using an overhead low shear mixer 210 to prevent the formation of thermal gradients and to keep the coating solution in a homogenous state.

Figure 3:
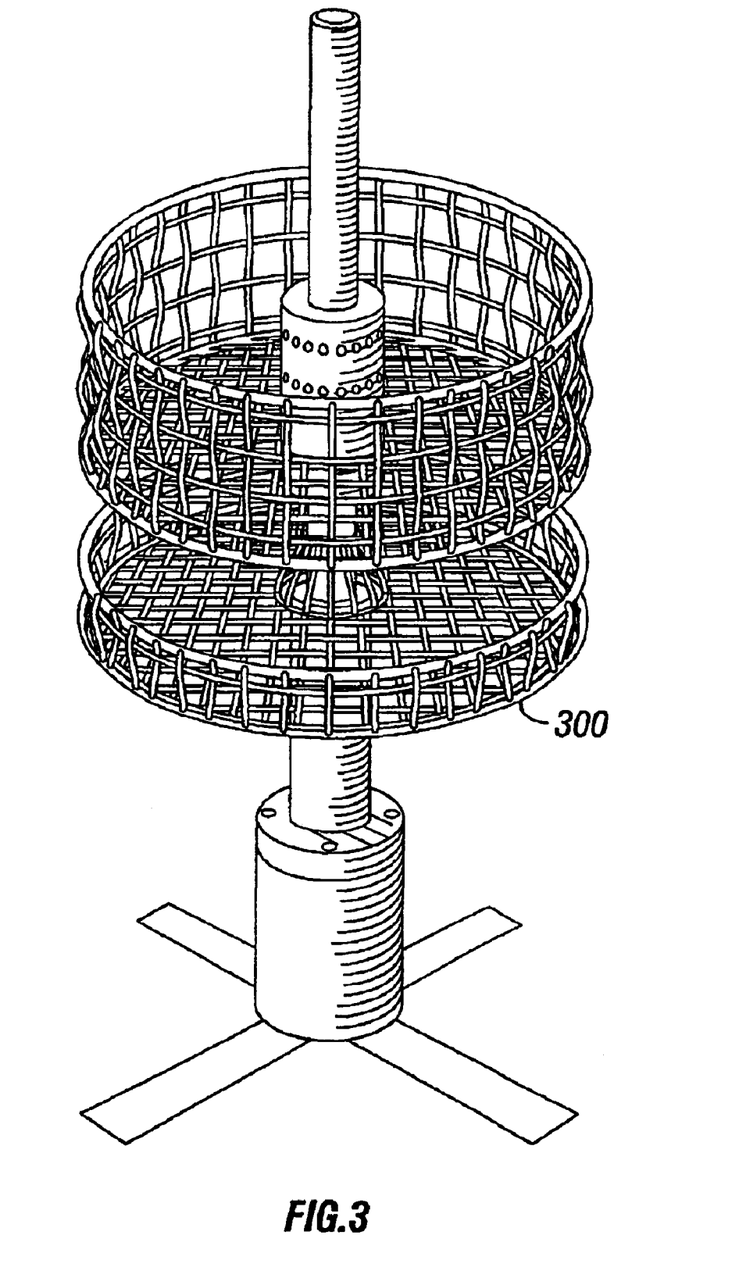
FIG. 3 depicts one embodiment of a product suspension device used in accordance with the teachings of the present invention.

Holding vessel 202 is fitted with a first sealable closure 212 that prevents solvent evaporation, minimizes contamination and reduces environmental exposure to the coating solution. Product to be coated is suspended in processing vessel 204 using devices and methods known to those skilled in the art. A non-limiting example of a product suspension device is depicted in FIG. 3 at 300. After the product has been securely loaded into processing vessel 204, second sealable closure 218 is secured. The proper sealing of closure 218 is detected by the process vessel closure sensor 220 that is in electronic communication with microprocessor/controller 216.

The coating cycle is initiated by engaging cycle initiate button 214 on microprocessor/controller 216. Microprocessor/control 216 will not allow the coating process to begin unless inputs from solvent temperature sensor 222, process vessel closure sensor 220 and process latch sensor 224 indicate the coating solution is at processing temperature and the process vessels closure 218 is closed and latched. The coating process begins as pre-heated coating solution is transferred from holding vessel 202 by pump/direction valve network 226 into process vessel 204.

The treatment timer 228 is activated when fluid level sensor 230 detects a level of coating solution sufficient to cover the product. At the initiation of the treatment period holding vessel 202 is isolated from circulation heater 206 and circulation cooler 232 begins circulating cooled heat transfer fluid through holding vessel's 202 thermal jacket. The coating solution in processing vessel 204 is maintained at coating temperature and continually mixed using a magnetically coupled mixer 234 located at process vessel's 204 base. Mixing maintains an even elevated temperature throughout the coating solution in the processing vessel and remains engaged as long as treatment timer 228 is active.

At the completion of the treatment period, pump/direction valve network 226 reverses direction and coating solution in process vessel 204 is pumped back into holding vessel 202. Circulation cooler 232 continues circulating cooled heat transfer fluid through holding vessel's 202 thermal jacket to cool returning coating solution to ambient temperature or below. After all remaining coating solution is removed from processing vessel 204 an aeration cycle is initiated.

During the aeration cycle gas passes through filter 242 and into processing vessel 204 through sparger (see FIG. 4 at 402) connector to process vessel's 204 bottom through gas line 246. The filtered gas passes over the coated product and out of process vessel 204 through gas line 244. High velocity gas regulator 236 that is responsive to microprocessor/controller 216 controls aeration gas flow velocity. The aeration period is regulated by aeration timer 238 located and under the control of microprocessor/controller 216. At the completion of the aeration cycle microprocessor/controller 216 shuts off the gas flow and engages wash fluid pump system 248 that provides wash fluid from wash fluid reservoir 250 to process vessel 204 though fluid supply line 252.

Wash fluid level is monitored by fluid level sensor 230 that is responsive to microprocessor/controller 216. After the preset wash fluid level is reached microprocessor/controller 216 shuts off wash fluid valve 248 and engages low velocity gas regulator 254. The low velocity gas flows through filter 242 and into processing vessel 204 through sparger (see FIG. 4 at 402) connector to process vessel's 204 bottom through gas line 246.

Wash timer 240 responsive to microprocessor/controller 216 regulates the wash interval. When wash timer 240 times out, microprocessor/controller 216 closes vent valve 260 and low velocity gas provided through sparger (see FIG. 4 at 402) pressurizes process vessel 204. Vessel out valve 256 and drain valve 258 are opened by the microprocessor/controller 216 and wash fluid exits processing vessel 204. The entire wash procedure can be repeated as many times as desired as herein described. The washed product can be removed from process vessel 204 at the completion of the wash step(s), or dried in sealed process vessel 204 using a high velocity air flow as describe for the aeration step above.

The present invention can be made from any assortment of materials compatible with the intended solutions and processes. In one embodiment of the present invention the holding vessel 202, processing vessel 204, and all associated metallic components that contact product or the coating solution are made entirely of stainless steel. Valve seats, seals, and fittings that contact coating solution are composed of, but not limited to Teflon® and Delrin®, (Teflon® and Delrin® are products made by E. I. du Pont de Nemours and Company of Wilmington, Del.).

The inventors of the present invention have determined that sparging gas into processing vessel 204 during one or more process steps 100 (FIG. 1), including, but not limited to post-coating, pre-wash step (aeration) 116, the washing process 118 and as an adjunct to drying 121 significantly improves coating consistency and appearance. Any number of gas sources can be used including, but not limited to air, nitrogen helium, argon or any combination therefore. In one embodiment of the present invention compressed air is provided to the coated products through a sparger 402 (FIG. 4) located near the bottom of processing vessel 204. Compressed gas passes through filter 242 having a mean porosity of between approximately 0.1 µm to 10 µm, preferably between approximately 0.5 µm and 2 µm, more preferably 0.7 µm to 1.0 µm, before entering sparger 402. The novel spiral shape of sparger 402 provides a vortex motion to the air current or wash fluid depending on the process cycle. The present inventors believe that the vortices significantly increases the sparger's efficiency and provides for a gentle, but thorough, agitation during the wash cycle.

The valves of the present invention that control the fluid and gas flow can be electronically or pneumatically activated. In one embodiment of the present invention the valves are pneumatically activated Teflon® seated ball valves. In other embodiments of the present invention electromechanical valves could be used. However, when potentially flammable solvents are used with the coating system of the present invention electromechanical valves present the potential for igniting the solvents. Consequently, the present inventors have chosen to use the more versatile and generally safer pneumatic activated valves. Electronic solenoid valves isolated in microprocessor/controller 216 control the pneumatically activated valves of the present invention. When a solenoid receives an output signal from microprocessor/controller 216 it opens, sending pressurized gas to the valves. The valves of the present invention remain open as long as pressurized gas flows to the valve. The gas flow is shut off and the valve closes when the output device controlling the valve receives a close command from the microprocessor/controller 216.

Figure 5:
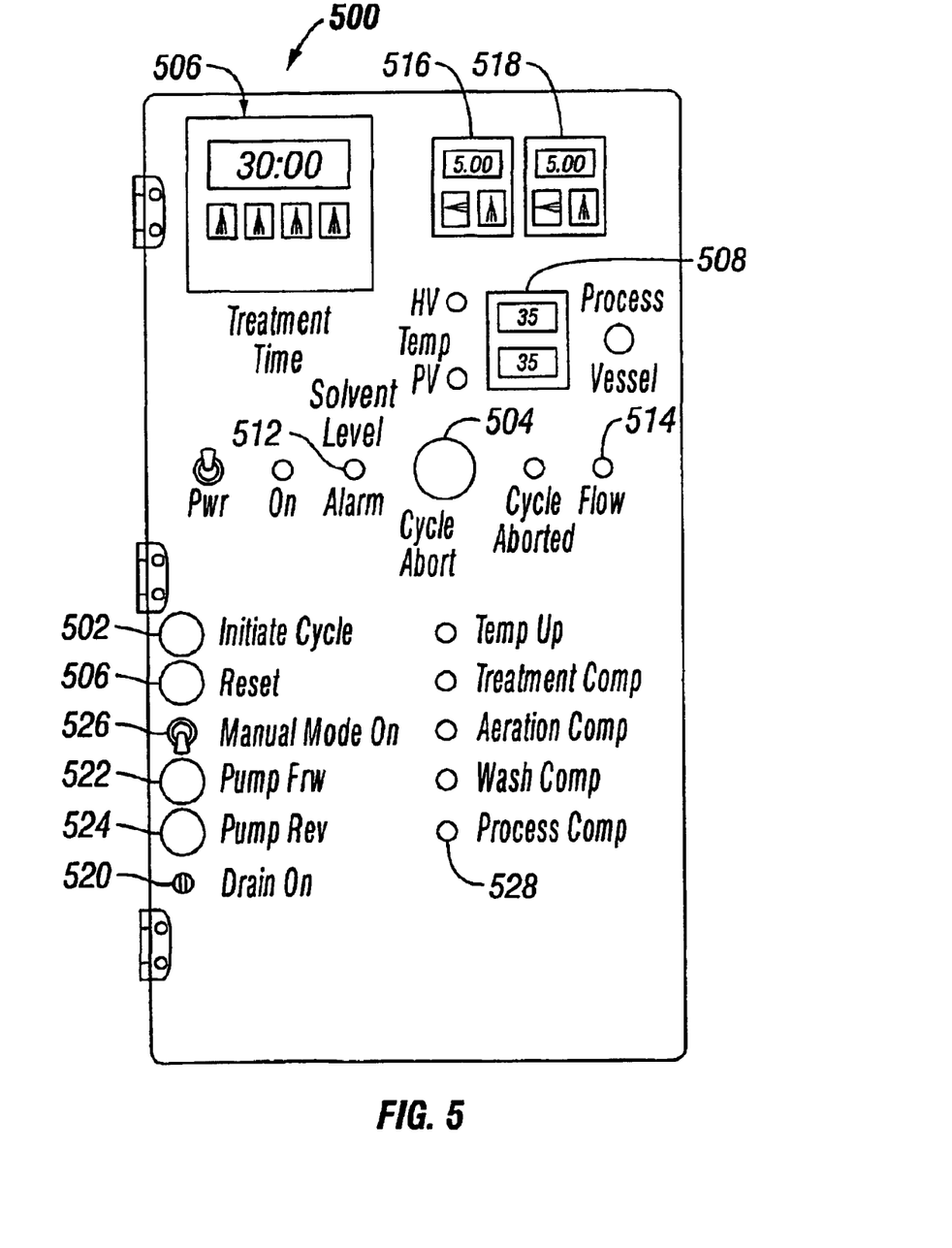
FIG. 5 depicts the control panel of the microprocessor/controller of the present invention.

Turning now to FIG. 5. The microprocessor/controller of the present invention can be any programmable microprocessor known to those of ordinary skill in the art that can receive, process, store and relay data to and from remote sensors and electromechanical devices. The microprocessor/controller inputs of the present invention include, but are not limited to, cycle start button 502, cycle abort button 504, treatment timer 506, solvent temperature 508, reset button 510, process level sensor 512, high level sensor, solution flow sensor 514, aeration timer 516, wash timer 518, manual drain key switch 520, process vessel cover sensor, process vessel latch sensor, manual pump forward 522, manual pump reverse 524, manual pump mode 526. The inputs depicted in FIG. 5, and other inputs of microprocessor/controller 500 can include any number of different options depending on the functions that are to be automated and conditions to be monitored.

Once data has been received and processed by microprocessor/controller 500 output devices responsive to microprocessor/controller 500 control the coating system 200 (FIG. 2) and coating process 100 (FIG. 1). Output devices of the present invention can be any type known to those of ordinary skill in the art. The output commands used to control the coating system 200 (FIG. 2) of the present invention include, but are not limited to, pump motor on/off, pump motor direction valves, holding vessel out valve, process vessel out valve, low pressure drain gas supply, drain valve open/closed, holding vessel to processing vessel vent, process complete indicator 528, sight glass vent valve, wash fluid on, reset hold signal for treatment timer, circulation cooler/heater control, aeration valve on, main system vent, aeration timer enable, wash timer enable.

The inputs and outputs of the present invention work in a coordinated fashion to control and monitor the coating system and process of the present invention. Table 1 illustrates the coordinated interaction of the inputs and outputs of one embodiment of the present invention. It is understood that there are many other input/output combinations and those presented in Table 1 are not meant to limit the present invention, but merely to provide one example. The corresponding input and output abbreviations used in Table 1 are defined in Tables 2 and 3 immediately following Table 1.

TABLE I

| Step | Process Step Description | Inputs On | Outputs On |
|---|---|---|---|
| 0 | Standby, vessels closed, rest | I-3, II-3, II-4 | II-2 |
| 1 | Start cycle, pump to process vessel | I-0 mom, I-3, II-3, II-4 | I-0, I-1, I-2, I-3, I-6, II-2 |
| 2 | Process level reached, processing | I-3, I-5, II-3, II-4 | I-1, II-3 |
| 3 | Process time elapsed, pumping back to HV | I-2, I-7, II-3, II-4 | I-0, I-2, I-3, I-6, II-3 |
| 4 | Back to holding vessel, aeration time on | I-2, II-3, II-4 | II-0, II-3, II-4, II-5, II-6 |
| 5 | Aeration done, rinse water fill to level | I-2, II-0, II-3, II-4 | II-1, II-3, II-5, II-6 |
| 6 | Full, bubble wash time | I-2, I-5, II-0, II-3, II-4 | II-3, II-4, II-5, II-6, II-7 |
| 7 | Dump rinse, blow down | I-2, II-0, II-1, II-3, II-4 | I-3, I-4, I-5, II-3, II-6, II-7 |
| 8 | Refill rinse to level | I-2, II-0, II-3, II-4 | I-5, II-1, II-3, II-5, II-6 |
| 9 | Full, 2$^{nd}$ wash cycle | I-2, I-5, II-0, II-3, II-4 | I-5, II-3, II-4, II-5, II-6, II-7 |
| 10 | Dump 2$^{nd}$ rinse, blow down | I-2, II-0, II-1, II-3, II-4 | I-3, I-4, I-5, II-3, II-6, II-7 |
| 11 | Cycle complete, in process dry cycle on | I-2, II-0, II-1, II-3, II-4 | I-4, I-5, I-7, II-3, II-5, II-6, II-7 |
| 12 | Process cycle complete, vessel open | I-2, II-0, II-1 | I-5, I-7, II-3, II-6, II-7 |
| 13 | Controller reset, cover open, temp low | I-4 mom (reset in) | I-2 |

NOTES:
Step 2  Input I-3 (Temp Alarm Off) may go off momentarily due to reaction time of the cold process vessel sensor being warmed by the incoming solution.
Step 3  Input I-3 (Temp alarm Off) may be On or Off due to cooling of the Holding Vessel. Controller becomes a HV temp monitor only.
Step 4  Inputs I-5 and I-6 (Sightglass Sensors) may be on due to condensation in the sightlglass during the first minutes of aeration time.

TABLE II

| Input No. | Description |
|---|---|
| I-0 | Start Cycle |
| I-1 | Abort Cycle |
| I-2 | Treatment Timer Time Out |
| I-3 | Solution Temp Input |
| I-4 | Reset Controller |
| I-5 | Reactor Vessel Process Point Solution Sensor |
| I-6 | Reactor Vessel High Solution Sensor |
| I-7 | Solution Flow Switch |
| II-0 | Aeration Timer Time Out |
| II-1 | Bubble Wash Timer Time Out |
| II-2 | Manual Drain Valve On |
| II-3 | Process Vessel Cover Closed |
| II-4 | Process Vessel Latched |
| II-5 | Manual Pump On (Forward Direction) |
| II-6 | Manual Pump On (Reverse Direction) |
| II-7 | Manual Pump Mode On |

TABLE III

| Output No. | Description |
|---|---|
| I-0 | Pump Motor On |
| I-1 | Pump Motor Direction (ON = Fwr) V[1] 1 & V2 |
| I-2 | Holding Vessel Valve On, V5 |
| I-3 | Process Vessel Valve On, V6 |
| I-4 | Low Pressure Drain Air Valve (Blow Down), V10 |
| I-5 | Drain Valve On, V4 |
| I-6 | Hld. V. to Pro. V. Vent Valve On, V7 |
| I-7 | Process Complete Indicator |
| II-0 | Sightglass Vent Valve On, V16 |
| II-1 | Pure Water Valve On, V11 |
| II-2 | Reset Treatment Timer |
| II-3 | HV Switch from Circ. Htr. to Cooler (Rly-2). Circ. Htr. Control to PV. Rly-1 |
| II-4 | Aeration Valve On, V8 |
| II-5 | Roof Vent (Exhaust) Valve, V3 |
| II-6 | Aeration Timer Enable |
| II-7 | Bubble Wash Timer Enable |

[1]V is an abbreviation for valve and refers to the pneumatic operated ball valves used in one embodiment of the present invention.

Figure 4:
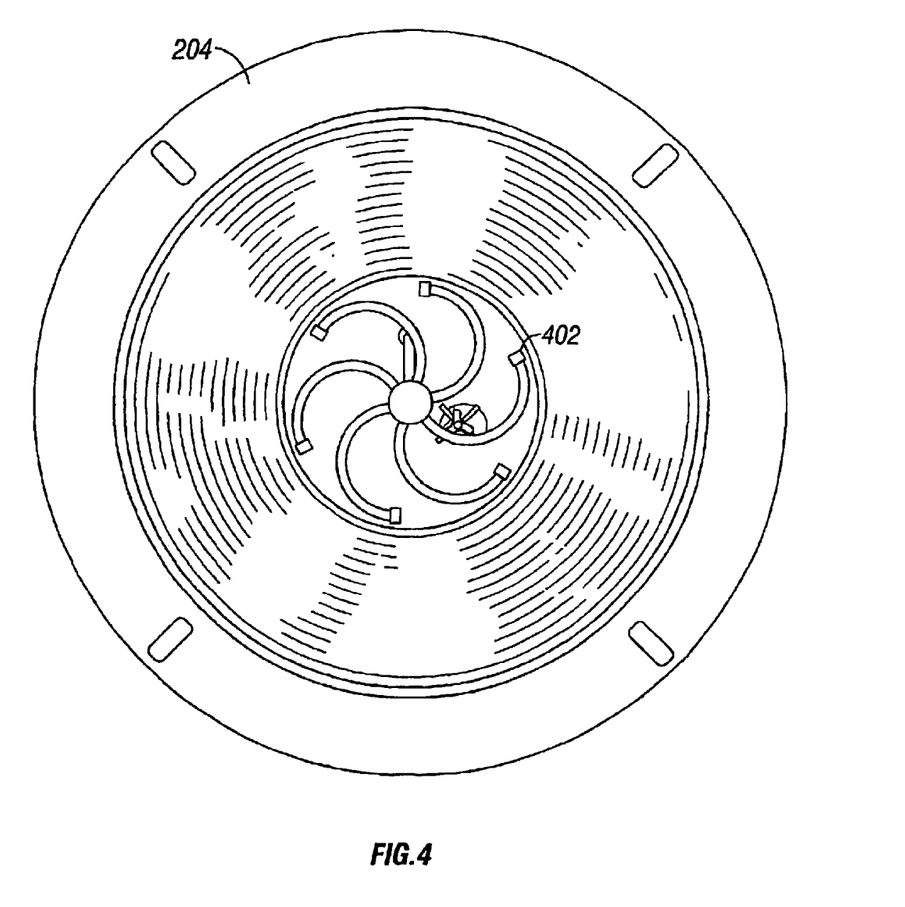
FIG. 4 depicts one embodiment of the gas sparger used in accordance with the teachings of the present invention.
Figure 6:
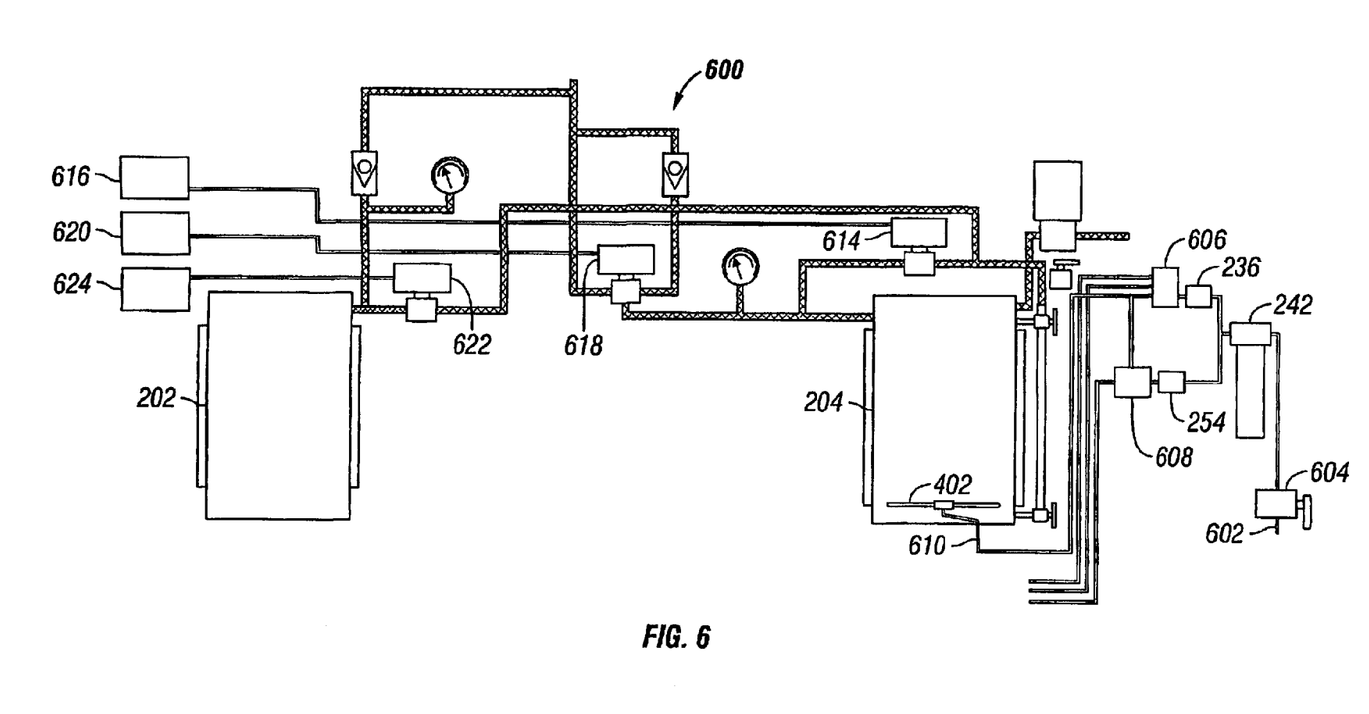
FIG. 6 depicts the compressed gas flow and gas vents used in one embodiment of the present invention.

FIG. 6 depicts compressed gas flow and the gas vents used in one embodiment of the present invention. Compressed air 600 is provided to coating system 200 (FIG. 2) through air line 602 when valve 604 is opened. Compressed air then moves through filter 242 and into either high pressure regulator 236 and through high pressure compressed air valve 606, or through low pressure regulator 254 and through low pressure valve 608 to sparger line 610 to provide compressed air to sparger 402 in processing vessel 204.

Coating solution is pumped from holding vessel 202 to processing vessel 204 and air is displaced from processing vessel 204 and sight glass 612 through sight glass vent valve 614. Sight glass valve 614 opens in response to solenoid 616 located in microprocessor/controller 216 (FIG. 2) and air is vented out of the system through vent 618 responsive to solenoid 620. Wash solution is purged from process vessel 204 by closing sight glass vent valve 614 while maintaining air flow into processing vessel 204 through sparger line 610. Air contained in holding vessel 202 is released therefrom as the coating solution is pumped from processing vessel 204 through holding vessel 202 to processing vessel vent 622 in response to solenoid 624.

Figure 7:
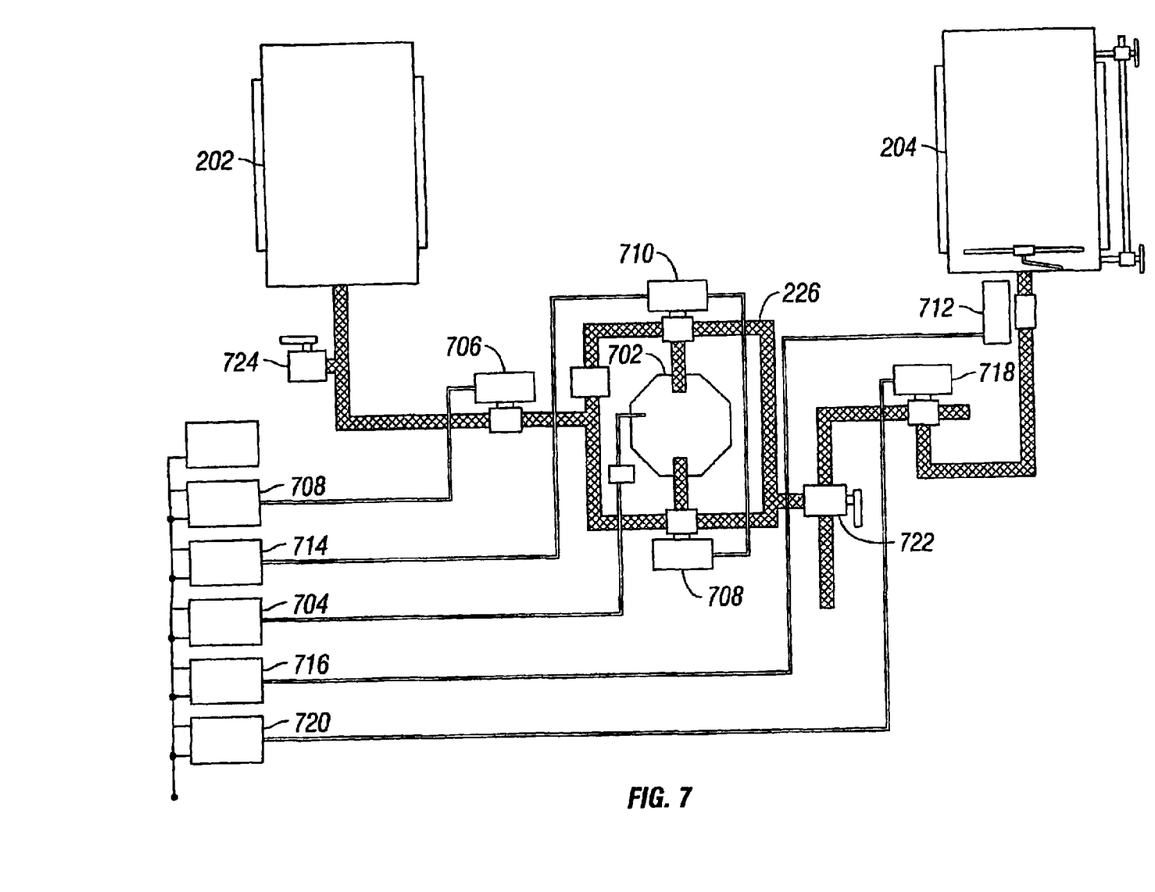
FIG. 7 schematically depicts coating solution transfer between the holding vessel and processing vessel in accordance with the teachings of the present invention.

FIG. 7 schematically depicts coating solution transfer between holding vessel 202 and processing vessel 204. Microprocessor/controller 216 initiates coating solution transfer following engagement of cycle start button 502 (FIG. 5). Solvent transfer pump 702 is activated by solenoid 704 and begins pumping coating solution from holding vessel 202 through holding vessel valve 706 in response to solenoid 708. The coating solution is pumped through pump direction valve 708 and directed towards processing vessel 204 by pump direction valve 710. Pump direction valves 708 and 710 are responsive to solenoid 714. Coating solution enters processing vessel 204 through processing valve 712 that is activated by solenoid 716. Coating solution returns to holding vessel 202 by reversing its path through pump/direction valve network 226. Drain valve 718, responsive to solenoid 720 directs coating solution flow to and from processing vessel valve 712, or can be engaged to direct wash fluids from processing vessel 204. Manual valve 722 can be engaged to drain spent coating solution from the coating system of the present invention and sample port valve 724 can be manually opened to withdraw coating solution samples for analysis. It is understood that FIG. 7 represents one embodiment of the coating solution transfer system of the present invention and that many other combinations of pumps and valves known to those of ordinary skill in the art can be employed.

Many of the solvents used in association with the coating system of the present invention can be toxic and/or flammable. Therefore, the present invention has a number of safety features. In one embodiment of the present invention a spill containment platform is integrated into the coating system. The holding vessel, processing vessel, fluid transfer systems, temperature controllers, gas vents and all fluid transfer lines are contained within the perimeter of a tray-like platform having high wall sides. The platform walls are high enough to safely contain the entire combined contents of the holding vessel, the processing vessel and solutions contained within the fluid transfer systems. In the unlikely event that a spill should occur, the manufacturing environment itself would not be contaminated.

In another embodiment of the present invention the coating system is provided with a series of fail safe devices composed of sensors that feed back to the microprocessor/controller. Sensor locations include, but are not limited to, holding vessel and processing vessel closures and latches, fluid level minimums and maximums, valves and vents. If the microprocessor/controller of the present invention does not receive the appropriate inputs from each sensor, the process will either fail to be initiated or aborted. Moreover, the microprocessor/controller of the present invention is provided with a prominent, easily accessible manual override that permits the operator to shut the system down should a potentially unsafe condition arise.

EXAMPLES

Example 1

Preparation of an Antimicrobial Coating Solution

Transfer 9.06 liters of acetone-free absolute methyl alcohol (catalogue number M 1775, Sigma Chemicals, St. Louis, Mo. USA) into the holding vessel of the present invention and engage the holding vessel mixer. Slowly add 681.3 grams of USP grade Rifampin (Lupin Laboratories, LTD, Mumbai, India) to the methanol. Next, add 568 grams of USP grade Minocycline (Companhia Industrial Produtora de Antibioticos, S. A., Castanheira Do Ribatejo, Portugal) to the Rifampin/methyl alcohol mixture. After all of the Rifampin and Minocycline have disolved, slowly added 13.63 liters of ACS reagent grade n-butyl acetate (catalogue numner B 6408 Sigma Chemicals, St. Louis, Mo. USA). Immediately cover the holding vessel and secure.

Example 2

Exemplary Coating Procedure Including Microprocessor/Contoller Input/Output Sequence Process Step 0:
Coating System Status: Stand-by condition, process vessel loaded, closed and latched. Vessel temperature 35° C.
Input[2] Status:
  1. Solvent Temperature Alarm off signal from temperature controller. I-3
  2. Process Vessel cover closed sensor signal. II-3
  3. Process Vessel cover latched sensor signal. II-4
[2] See Table 2.
Output[3] Status:
  1. Treatment Timer reset signal. II-2
[3] See Table 3.

Process Step 1
Coating System Status: Initiate process cycle, pumping solution to process vessel.
Input Status:
 1. Initiate Cycle push button signal (momentary). I-0
 2. Solvent Temperature Alarm off signal from temperature controller. I-3
 3. Process Vessel cover closed sensor signal. II-3
 4. Process Vessel cover latched sensor signal. II-4
Output Status:
 1. Solvent Pump On. I-0
 2. Pump direction signal out, (pump to process vessel from holding vessel). I-1
 3. Holding Vessel Output Valve Open. I-2
 4. Process Vessel Output Valve Open. I-3
 5. Holding Vessel to Process Vessel Vent Valve on. I-6
 6. Treatment Timer reset signal. I-2
Process Description:
 To initiate the process cycle the microprocessor/controller must have inputs from the temperature controller (solution temperature is at process temperature), and the two process vessel cover sensors (cover closed and latched). Once these inputs are present, the initiate cycle button will start the process cycle.
 The controller then turns on the solvent pump, the two vessel output valves, the vessel to vessel vent valve, and the pump flow direction valves so the pump direction is from holding vessel to process vessel.
Process Step 2
Coating System Status: Solvent process level reached in process vessel, processing
Input Status:
 1. Solvent Temperature Alarm off signal from temperature controller. I-3
 2. Process Vessel Solvent Level Sensor signal. I-5
 3. Process Vessel cover closed sensor signal. II-3
 4. Process Vessel cover latched sensor signal. II-4
Output Status:
 1. Pump direction signal out, (pump to process vessel from holding vessel). I-1
 2. Heat control/flow switches to process vessel, stir motor on. Holding vessel (cool) II-3
Process Description:
 When the solution level reaches the sight glass level sensor, a signal is sent to the microprocessor/controller indicating that the process solution level has been reached. The microprocessor/controller turns off the pump, the vessel output valves, and the vessel to vessel vent valve, but leaves the pump direction valve in the holding vessel to process vessel position. The microprocessor/controller turns off the reset signal to the treatment timer allowing the timer to start timing. The microprocessor/controller also switches the valves that disconnect the circulation heater flow from the process holding vessel and maintains flow to the processing vessel. The microprocessor/controller then initiates the holding vessel cooling cycle. The magnetic stir unit motor is engaged and the circulation temperature controller switches to monitor the process vessel temperature.
Process Step 3
Coating System Status: Process time elapsed, pumping solvent back to holding vessel.
Input Status:
 1. Cycle Timer Timed Out signal. I-2
 2. Solvent Flow Switch Output Signal. I-7
 3. Process Vessel cover closed sensor signal. II-3
 4 Process Vessel cover latched sensor signal. II-4
Output Status:
 1. Solvent Pump On. I-0
 2. Holding Vessel Output Valve Open. I-2
 3. Process Vessel Output Valve Open. I-3
 4. Holding Vessel to Process Vessel Vent Valve On. I-6
 5. Circulation heater to process vessel, circulation cooler to holding vessel. II-3
Process Description:
 When the Treatment timer reaches zero, a time-out signal is sent to the microprocessor/controller. The process vessel stir motor turns off. Circulation heater flows only to the process vessel.
 The circulation heater temperature controller begins monitoring and displaying the holding vessel temperature. The output signal is opened so the heater element in the circulation heater turns off The microprocessor/controller turns on the pump, the vessel output valves, and the vessel to vessel vent valve.
 During the first three seconds of pumping, an internal microprocessor/controller timer delays the flow switch signal so the pump has time to start solution flow and activate the flow switch. The flow switch becomes active when the three second timer times out. When all of the solution is pumped back into the holding vessel, the pump starts pumping air. The flow switch signals the microprocessor/controller and starts the aeration cycle and timer. The microprocessor/controller starts a 10 second pump off delay timer. This pump off delay purges the air sparger of solvent and allows 10 seconds for the pump to pump the sparger purge solvent to the holding vessel. At the end of the 10 second delay, the controller turns the pump, the vessel output valves, and the vessel to vessel vent valves off
Process Step 4
Coating System Status: Solvent Back to Holding Vessel, Aeration Time.
Input Status:
 1. Cycle Timer Timed Out signal. I-2
 2. Process Vessel cover closed sensor signal. II-3
 3. Process Vessel cover latched sensor signal. II-4
Output Status:
 1. Sight lass Vent On. II-0
 2. Circulation heater to process vessel, circulation cooler to holding vessel. II-3
 3. Aeration Valve On. II-4
 4. Roof Vent Valve On. II-5
 5. Aeration Timer Enable. II-6
Process Description:
 As stated in the step 3 description, the loss of the flow switch signal causes the controller to start the aeration cycle. The controller turns on the high flow air valve, the roof vent valve, and the aeration timer enable signal. The aeration timer starts timing. The Sight Glass vent turns on at the end of the pump purge delay time. At the end of the sparger purge 10 second pump off delay, the pump and solution line valves turn off.
Process Step 5
Coating System Status: Aeration time elapsed, fill process vessel with wash water.
Input Status:
 1. Cycle timer timed out signal. I-2
 2. Aeration Timer Time Out Signal. II-0
 3. Process Vessel cover closed sensor signal. II-3
 4. Process Vessel cover latched sensor signal. II-4
Output Status:
 1. Pure Water Valve On. II-1
 2. Circulation heater to process vessel, circulation cooler to holding vessel. II-3

3. Roof Vent Exhaust Valve On. II-5
3. Aeration Timer Enable On. II-6

Process Description:

When the aeration timer reaches zero, a signal is sent to the microprocessor/controller, turning sight glass vent valve off, and turning on the distilled water valve. The vessel fills with pure water until the water level reaches the process level sensor on the sight glass.

Process Step 6

Coating System Status: Process vessel fill of wash water to process level, bubble wash on.

Input Status:
 1. Cycle Timer Timed Out signal. I-2
 2. Process Vessel Process Level Sensor Signal. I-5
 3. Aeration Timer Time Out Signal. II-0
 4. Process Vessel cover closed sensor signal. II-3
 5. Process Vessel cover latched sensor signal. II-4

Output Status:
 1. Circulation heater to process vessel, circulation cooler to holding vessel. II-3
 2. Aeration Air Valve On. II-4
 3. Roof Vent Exhaust Valve On. II-5
 4. Aeration Timer Enable On. II-6
 5. Wash Timer Enable Signal. II-7

Process Description:

When the level reached signal from the process level sensor reaches the microprocessor/controller the water valve is turned off and the wash timer is enabled. The aeration valve, and the roof vent valve remain on to bubble wash the product.

Process Step 7

Coating System Status: Wash Time elapsed, Drain Process Vessel of wash water.

Input Status:
 1. Cycle Timer Timed Out signal. I-2
 2. Aeration Timer Time Out Signal. II-0
 3. Wash Timer Time Out Signal. II-1
 4. Process vessel cover closed sensor signal. II-3
 5. Process Vessel cover latched sensor signal. II-4

Output Status:
 1. Process Vessel Out Valve. I-3
 2. Low Pressure Drain Air Valve On. I-4
 3. Drain Valve On. I-5
 4. Circulation heater to process vessel, circulation cooler to holding vessel. II-3
 5. Aeration Timer Enable On. II-6
 6. Wash Timer Enable Signal. II-7

Process Description:

When the wash timer reaches zero, a signal is sent to the microprocessor/controller. The microprocessor/controller turns off the high flow air valve and the roof vent valve, and turns on the low pressure air valve, process vessel output valve, and drain valve. Low pressure air blows the wash water to drain. The controller also initiates a five minute interval timer. When the internal timer times out, the microprocessor/controller turns the low pressure air and the vessel out valve off and activates a one second reset timer that resets the wash and drain timers. The three way drain valve remains in the drain position for the second wash. Process steps 5–7 repeat for a second wash/drain cycle. The reset timer disables the reset function after the first reset so the controller will end the process cycle after the second wash/drain cycle.

Process Step 8, Repeat process steps 5, with output I-5 (drain valve) on.

Process Step 9, Repeat process step 6, with output I-5 (drain valve) on.

Process Step 10, Repeat process step 7

Process Step 11

Coating System Status Process Cycle Complete, Dry Cycle On

Input Status:
 1. Treatment Timer time Out. I-2
 2. Aeration Timer Time Out. II-0
 3. Wash Timer Time Out. II-1
 4. Process Vessel Closed Signal. II-3
 5. Process Vessel Cover Latched Signal. II-4

Output Status:
 1. Low Press Drain Air On. I-4
 2. Drain Valve. I-5
 3. Process Complete Indicator Lamp. I-7
 4. Circulation Cooler/Heater Flow Control. II-3
 5. Roof Vent On. II-5
 6. Aeration Timer Enable. I-6
 7. Wash Timer Enable. I-7

Process Description:

With the 1 second Wash/Drain cycle timed out and latched, the microprocessor/controller does not reset the wash/drain cycle and the process is complete. The latched reset timer output turns on the process complete lamp at the end of the second wash/drain cycle. The low pressure drain air remains on and the roof vent opens to dry parts in the processing vessel.

Process Step 12

Coating System Status: Process Cycle Complete, Process Vessel Open, Remove Product.

Input Status:
 1. Treatment Timer Time Out. I-2
 2. Aeration Timer Time Out Signal. II-0
 3. Wash Timer Time Out Signal. II-1

Output Status:
 1. Drain Valve. I-5
 2. Process Complete Indicator Lamp On. I-7
 3 Circulation heater to processing vessel circulation cooler to holding vessel. II-3
 4. Aeration Timer Enable On. II-6
 5. Wash Timer Enable Signal. II-7

Process Description:

Unlatching the process vessel when removing product turns off the roof vent and the low pressure drain.

Process Step 13 Controller Reset

Input Status:
 1. Reset Signal (momentary)

Output Status:
 1. Reset Signal (Momentary)

Process Description:

The reset signal resets the program to the standby mode. The circulation cooler turns off and is disconnected from the holding vessel. Circulation heater flow switches back to both holding and processing vessels. Process temperature for the next coating process.

From the foregoing description, one skilled in the art can readily ascertain the essential characteristics of the invention and, without departing from the spirit and scope thereof, can adapt the invention to various usages and conditions. Changes in the form and substitution of equivalents are contemplated as circumstances may suggest or render expedient, and although specific terms have been employed herein, they are intended in a descriptive sense and not for purposes of limitation. Furthermore, any theories attempting to explain the mechanism of actions have been advanced merely to aid in the understanding of the invention and are not intended as limitations, the purview of the invention being delineated by the following claims.

We claim:

1. A semi-automated medical device coating system comprising:
a first vessel having a sealable cover, at least one mixing device and at least one heat transfer device; a second vessel for coating material having a sealable cover, at least one mixing device and at least one heat transfer device, said second vessel in two-way fluid communication with said first vessel; a fluid transfer system adapted to transfer fluids between said first and said second vessels; a support adapted to suspend a device in said second vessel; and a gas operated sparger in said second vessel adapted to transfer gas from an external gas supply into said second vessel.

2. The semi-automated medical device coating system of claim 1 wherein said coating system is a closed system substantially preventing exposure of said fluid to the ambient atmosphere or light.

3. The semi-automated medial device coating system of claim 1 further comprising a plurality of sensors cooperatively connected to said first vessel, said second vessel, said fluid transfer system, said heat transfer devices and said mixers, said sensors responsive to at least one microprocessor/controller.

4. The semi-automated medical device coating system of claim 1 further comprising at least one temperature controller responsive to at least one microprocessor/controller for heating and cooling said heat transfer device of said first and said second vessels.

5. The semi-automated medical device coating system of claim 1 wherein said fluid transfer system is at least one pump.

6. The semi-automated medical device coating system of claim 1 wherein said sparger is a spiral shaped device located within said second vessel.

7. A semi-automated implantable medical device coating system comprising: a containment platform having at least one temperature controller; a holding vessel fixed to said containment platform having a first sealable closure, at least one mixer and a first heat transfer device in cooperation with said at least one temperature controller; a processing vessel for coating material said processing vessel fixed to said containment platform having a second sealable closure, a gas sparger, at least one mixer, a support for suspending said implantable medical device within said processing vessel and a second heat transfer device in cooperation with said at least one temperature controller; a first fluid transfer system in cooperation with said containment platform adapted to transfer fluids between said holding vessel and said processing vessel; a second fluid transfer system in cooperation with said containment platform adapted to transfer fluid between said processing vessel and a remote fluid reservoir and a waste reservoir; a gas reservoir in cooperation with said gas sparger; a plurality of valves in cooperation with said first and said second fluid transfer systems and said gas reservoir; a plurality of sensors in cooperation with said holding vessel, said processing vessel, said first and said second sealable closures, said first and said second heat transfer devices, said first and said second fluid transfer systems, said plurality of valves and said at least one temperature controller; a programmable controller responsive to said plurality of sensors.

8. The semi-automated implantable medical device coating system of claim 7 wherein said programmable controller is adapted to regulate the contents, temperatures, fluid levels, and gas flow within said holding vessel and said processing vessel.

9. The semi-automated implantable medical device coating system of claim 7 wherein said programmable controller is adapted to open and close said plurality of valves.

10. The semi-automated implantable medical device coating system of claim 7 wherein said programmable controller is adapted to act as a fail-safe monitor responsive to said plurality of sensors.

11. A semi-automated medical device coating system comprising: a coating solution holding vessel; a processing vessel for coating medical devices separate form said coating solution vessel; a coating solution transfer system; a heat transfer system for heating and cooling said holding vessel and said processing vessel either simultaneously or separately; a mixer associated with said holding vessel and said mixing vessel; at least one remote sensor; at least one microprocessor/controller for receiving data from said at least one remote sensor and for transmitting information to said coating solution transfer system and said heat transfer system; a product suspension device for holding said medical device in place during coating, a wash solution reservoir; a wash solution transfer system; at least one valve; and at least one vent.

12. A medical device coating system comprising: a first receptacle, said receptacle comprised of a material capable of holding an antimicrobial substance without introducing contamination; an antimicrobial substance received initially in said first receptacle a second receptacle in fluid communication with said first receptacle; said fluid communication being substantially closed to ambient air at least during flow of fluid; said second receptacle sized and shaped to receive at least one medical device; and an electronic controller to govern flow between said first receptacle and said second receptacle wherein the antimicrobial substance is coated and remains on the at least one medical device when the at least one medical device is received in the second receptacle.

13. A medical device coating system comprising: a first receptacle, said receptacle comprised of a material capable of holding an antimicrobial substance without introducing contamination; an antimicrobial substance received initially in said first receptacle; a second receptacle in fluid communication with said first receptacle; said fluid communication being substantially closed to ambient air at least during flow of fluid; said first receptacle and said second receptacle being continually maintained under an inert gas; said second receptacle sized and shaped to receive at least one medical device; and an electronic controller to govern flow between said first receptacle and said second receptacle wherein the antimicrobial substance is coated and remains on the at least one medical device when the at least one medical device is received in the second receptacle.

* * * * *